United States Patent
Soldato

(10) Patent No.: US 7,378,437 B2
(45) Date of Patent: May 27, 2008

(54) DRUGS FOR DIABETES

(75) Inventor: Piero Del Soldato, Milan (IT)

(73) Assignee: NICOX S.A., Sophia Antipolis-Valbonne (FR)

( * ) Notice: Subject to any disclaimer, the term of this patent is extended or adjusted under 35 U.S.C. 154(b) by 0 days.

(21) Appl. No.: 10/398,511

(22) PCT Filed: Oct. 9, 2001

(86) PCT No.: PCT/EP01/11665

§ 371 (c)(1),
(2), (4) Date: Apr. 11, 2003

(87) PCT Pub. No.: WO02/30867

PCT Pub. Date: Apr. 18, 2002

(65) Prior Publication Data

US 2004/0023890 A1 Feb. 5, 2004

(30) Foreign Application Priority Data

Oct. 12, 2000 (IT) .......................... MI2000A2201

(51) Int. Cl.
*A61K 31/40* (2006.01)
*A61K 31/44* (2006.01)
*A61K 31/21* (2006.01)

(52) U.S. Cl. ...................... 514/413; 514/357; 514/509; 514/866

(58) Field of Classification Search ................. 514/413, 514/509, 866
See application file for complete search history.

(56) References Cited

U.S. PATENT DOCUMENTS

| 4,452,806 | A | * | 6/1984 | Rizzi et al. | .................. | 514/391 |
| 5,518,998 | A | * | 5/1996 | Backstrom et al. | ............ | 514/3 |
| 5,597,847 | A | * | 1/1997 | Matji et al. | .................. | 514/509 |
| 5,861,426 | A | * | 1/1999 | Del Soldato et al. | ....... | 514/413 |
| 6,040,341 | A | * | 3/2000 | Del Soldato et al. | ....... | 514/509 |
| 6,054,587 | A | * | 4/2000 | Reddy et al. | ................ | 548/113 |
| 6,211,233 | B1 | * | 4/2001 | Del Soldato | ................ | 514/509 |
| 6,613,784 | B1 | * | 9/2003 | Benedini et al. | ............. | 514/357 |

FOREIGN PATENT DOCUMENTS

EP 0 578 494 A1 1/1994
WO 00/61537 * 10/2000

OTHER PUBLICATIONS

Bailey "Potential new treatments for type 2 diabetes", Trends in Pharm. Sci., vol. 21, pp. 259-265, 2000.
"Antidiabetic Agents", Martindale, the Extra Pharmacopoeia, pp. 342-343, 1996.
The Merck Index, XII Ed., 1996.
Nenseter, et al., "Paracetamol Inhibits Copper Ion-Induced, Azo Compound-Initiated, and Mononuclear Cell-Mediated oxidative Modification of LDL", Atheroscler, Thromb. 15, pp. 1338-1344, 1995.
Facino et al., "Hydroxynimesulide, The Main Metabolite of Nimesulide, Prevents Hydroperoxide Hemoglobin-Induced Hemolysis of Rat Erythrocytes", Drugs Exptl. Clin. Res. XXIII (5/8), pp. 157-165, 1997.
Greene, "Protective groups in organic synthesis", Harward University Press, 1980.
Remington's Pharmaceutical Sciences, 15th Edition.
Physician's Desk Reference.
Katakam et al., "Endothelial dysfunction precedes hypertension in diet-induced insulin resistance", Am. J. Physiol. 275, R788-R792, 1998.
Tashima et al., "Lack of gastric toxicity of nitric oxide-releasing aspirin, NCX-4016, in the stomach of diabetic rats", Life Sciences 67: 1639-1652 (2000).

* cited by examiner

*Primary Examiner*—Kevin E. Weddington
(74) *Attorney, Agent, or Firm*—Arent Fox LLP

(57) ABSTRACT

Use for the diabetes treatment of compounds or salts thereof, having the following general formula (I): A-$(B)_{b0}$—$(C)_{c0}$—$NO_2$ wherein A contains the radical of a drug having an antiinflammatory or analgesic activity, B is a bivalent linking group wherein the precursor must meet the tests described in the application, C is a a bivalent linking group as defined in the invention.

10 Claims, No Drawings

DRUGS FOR DIABETES

The present invention relates to specific classes of compounds and their use for the diabetes treatment.

More specifically it relates to the treatment of type 2 diabetes.

As it is well known, conventionally diabetes is usually divided in two types: diabetes of type 1, which mainly appears in young people, and diabetes of type 2, which affects elderly people.

Diabetes of type 1 is successfully treated with insulin; while diabetes of type 2 is only partially effective towards the insulin therapy. The type 2 diabetes is the most frequent one, particularly in elderly people. About 18-20% of the population over 65 years suffers from it (National Diabetes. Data Group "Diabetes in America" $2^{nd}$ ed. Harris M. Ed. Bethesda, National Institutes of Health, 1995). By taking into account of the progressive ageing of the population (people over sixty-five now represent over 15% of the population) it is evident that the treatment of this disease represents a priority medical and social requirement.

Forms of diabetes also exist wherein the type 1 and 2 are contemporaneously present.

The insulin resistance has a significant clinical importance (Trends in Pharm. Sci. 21, 259-265, 2000) both in connection with the primary disease and its complications (vascular diseases, retinopathy, polyneuropathy, gastroenteropathy, nephropathy, etc.) (Martindale, The Extra Pharmacopoeia p. 342, 1996).

As it is specified also in a late publication (Trends in Pharm. Sci. 21, 259-265, 2000) the above requirement results still unsatisfied since no drug is able to effectively face the disease and its complications.

The drugs used in the diabetes therapy belong to the following therapeutic classes, defined on the basis of the pathogenetic role of the insulin resistance (Trends in Pharm. Sci. 21, 259-265 2000): insulin, sulphanylureas, metformin, inhibitors of alpha-glycosidase (acarbose) and thiazolidine diones (troglitazone).

Insulin is the most known drug and it is the reference one. The insulin therapy shows the following drawbacks:
- the drug is administrable only by parenteral route,
- it is necessary to constantly control the glycaemia levels,
- local allergic reactions can arise,
- the insulin resistance compells to meaningfully increase the drug dosage during the time,
- the local tolerability is poor.

Also the other therapeutical approaches are not without drawbacks, sometimes even remarkable. For example sulphanylureas, which are administered alone or in combination with insulin or with other oral hypoglycemizing drugs, can cause hypoglycemia. The metformin which is used alone or in combination with sulphanylurea, is contraindicated in the presence of renal and hepatic diseases, and can induce a state of lactic acidosis. Acarbose is used alone or in combination with sulphanylurea for reducing the postprandial glycemic levels, but it often induces side effects at the gastrointestinal system level. Troglitazone, which is only used in combination with insulin, can induce hepatotoxic effects.

The need was felt to have available drugs which could be administered to diabetic patients, also under treatment with hypoglycemizing drugs, preferably insulin, and able to increase the direct antidiabetic effect thereof, i.e. at pancreatic level, and to reduce the diabetes complications, in particular vascular diseases, retino-pathies, neuropathies, gastroenteropathies, nephropathies, etc.

It has now surprisingly and unexpectedly found that this technical problem can be solved with the class of drugs described hereunder.

An object of the present invention is the use in the diabetes treatment, preferably of type 2, of compounds or salts thereof, having the following general formula:

$$A\text{-}(B)_{b0}\text{---}(C)_{c0}\text{---}NO_2 \qquad (I)$$

wherein:
c0 is an integer and is 0 or 1;
b0 is an integer and is 0 or 1; with the proviso that at least one between c0 and b0 is different from zero;
$A=R\text{-}T_1\text{-}$, wherein
  R is the radical of a drug and
  $T_1=(CO)_t$ or $(X)_{t'}$, wherein $X=O$, S, $NR_{1C}$, $R_{1C}$ is H or a linear or branched alkyl having from 1 to 5 carbon atoms, t and t' are integers and equal to zero or 1, with the proviso that t=1 when t'=0;
  t=0 when t'=1;
$B=\text{-}T_B\text{-}X_2\text{-}T_{BI}\text{-}$ wherein
  $T_B$ and $T_{BI}$ are equal or different;
  $T_B=(CO)$ when the reactive function in the precursor drug is —OH or —$NH_2$; $T_B=X$, as above defined, when the reactive function in the precursor drug is —COOH;
  $T_{BI}=(CO)_{tx}$ or $(X)_{txx}$, wherein tx and txx have the value of 0 or 1; with the proviso that tx=1 when txx=0, tx=0 when txx=1; X is as above defined;
  $X_2$ is a bivalent linking group as defined below;
C is the bivalent radical -$T_C$-Y— wherein
  $T_C=(CO)$ when tx=0, $T_C=X$ when txx=0, X being as above defined; when b0 =1
  $T_C=CO$ when t=0, $T_C=X$ when t'=0, X being as above defined when b0=0;
Y is:
$Y_p$:

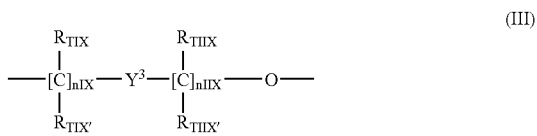

$$\begin{array}{cc} R_{TIX} & R_{TIIX} \\ | & | \\ \text{---}[C]_{nIX}\text{---}Y^3\text{---}[C]_{nIIX}\text{---}O\text{---} \\ | & | \\ R_{TIX'} & R_{TIIX'} \end{array} \qquad (III)$$

wherein:
  nIX is an integer in the range 0-3, preferably 1;
  nIIX is an integer in the range 1-3, preferably 1;
  $R_{TIX}$, $R_{TIX'}$, $R_{TIIX}$, $R_{TIIX'}$, equal to or different from each other are H or linear or branched $C_1$-$C_4$ alkyl; preferably $R_{TIX}$, $R_{TIX'}$, $R_{TIIX}$, $R_{TIIX'}$ are H.
  $Y^3$ is a saturated, unsaturated or aromatic heterocyclic ring containing one or two nitrogen atoms, having 5 or 6 atoms,
or Y can be:
$Y_O$, selected from the following:
  an alkylenoxy group R'O wherein R' is $C_1$-$C_{20}$ linear or branched when possible, preferably having from 2 to 6 carbon atoms, or a cycloalkylene having from 5 to 7 carbon atoms, in the cycloalkylene ring one or more carbon atoms can be substituted by heteroatoms, the ring can have side chains of R' type, R' being as above defined; or one of the following groups:

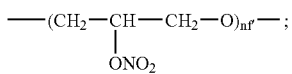

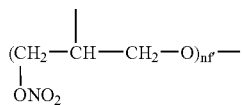

wherein nf' is an integer from 1 to 6 preferably from 1 to 4;

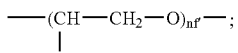

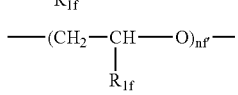

wherein $R_{1f}$=H, $CH_3$ and nf' is an integer from 1 to 6; preferably from 1 to 4;

or Y is $Y_{Ar}$ and is selected from the following:

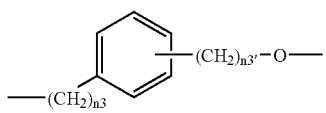

wherein n3 is an integer from 0 to 3 and n3' is an integer from 1 to 3;

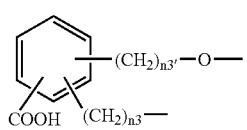

wherein n3 ed n3' have the above mentioned meaning, $X_2$, bivalent radical, is such that the corresponding precursor of B, $-T_B-X_2-T_{BI}-$ wherein the free valences of $T_B$ and $T_{BI}$ are each saturated with OZ, with Z or $-N(Z^I)(Z^{II})$, wherein Z=H, $C_1-C_{10}$, preferably $C_1-C_5$ alkyl, linear or branched when possible, $Z^I$, $Z^{II}$ equal or different have the Z value as above defined, depending on the fact that $T_B$ and/or $T_{BI}$=CO or X, in connection with the values of t, t', tx and txx;

when in formula (I) b0 =1 if the precursor of B as above defined meets test 4A and it does not meet test 5 as described hereunder, then c0=0;

if the precursor of B meets both tests 4A and 5, but it does not meet test 4 as described hereunder, then c0=0 or 1, and Y preferably is $Y_O$;

if the precursor of B meets test 4, then c0=1 and Y preferably is $Y_O$;

when in formula (I) b0=0, c0=1 and Y=$Y_p$ or $Y_{Ar}$;

R is the radical of a precursor drug having the following formula:

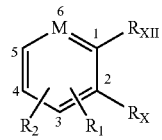

(AII)

wherein:

$R_{XII}$ is selected from the following:

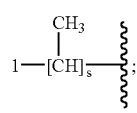

(AXL)

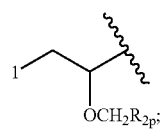

(AV)

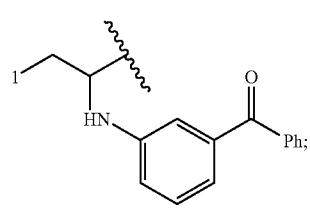

(AVI)

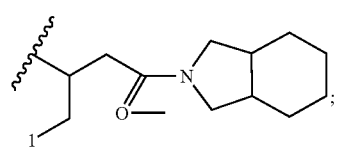

(AX)

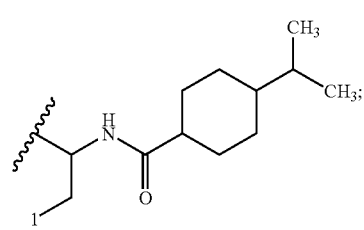

(ALVX)

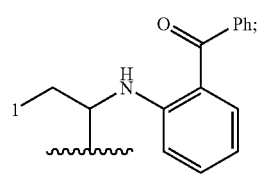

(ALXX)

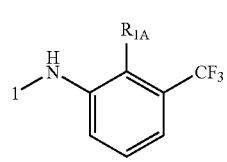

(AXX)

or $R_{XII}$ with $R_X$ forms the following radical:

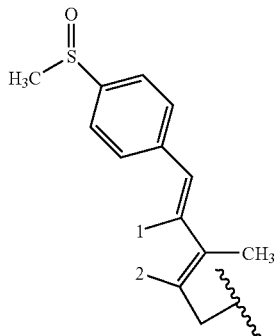
(AXXX)

wherein the bond between $R_{XII}$ and the carbon atom at position 1 of the ring of formula (AII) is indicated with: 1-($R_{XII}$), in formula (AXXX) it is shown the bonds of the carbon atoms at position 1 and 2 respectively with the radical formed by $R_{XII}$ combined with $R_X$; the symbol:

(δ)

in the formulas indicates the bond with $T_1$ of radical A of formula (I) above;

in formula (AXL) s is an integer and is zero or 1;

in formula (AV) $R_{2p}$ is $CH_3$, $CF_3$;

in formula (AXX) $R_{1A}$ is H, $CH_3$;

the substituent $R_X$ at position 2 of the ring of formula (AII) is present when $R_{XII}$ has a meaning different from (AXL); when there is $R_X$ there can not be $R_1$;

$R_X$ is H, or (δ) as above defined when $R_{XII}$ is the radical of formula (AXX); or it forms with $R_{XII}$ the radical of formula (AXXX);

the substituent $R_1$ is present when $R_{XII}$ has the meaning of (AXL); when there is $R_1$ there cannot be $R_X$ and wherein $R_1$ is at a position different from position 2, the carbon atom at position 2 is saturated with hydrogen; $R_1$ is H, $COOR_3$, $OCOR_3$, $CONHCOR_3$, $R_3$ being:

methyl, ethyl or linear or branched $C_3$-$C_5$ alkyl, an aromatic ring having 5 or 6 carbon atoms, preferably 6 carbon atoms, which can be optionally substituted in ortho, meta or para position with one or more groups, preferably one group, chosen from the following:

a radical a) chosen between H; OH; halogen preferably bromine or fluorine; $R_4$ an alkyl from 1 to 4 carbon atoms, linear or branched when possible; —$OR_4$; —$COR_4$; a linear or branched when possible pefluo-roalkyl from 1 to 4 carbon atoms, for example tri-fluoromethyl; nitro, —$NH_2$, —$NHR_4$, —$N(R_4)_2$, —$OSO_3H$, acetylamino; —$CONH_2$;, preferably one hydroxy group in position 2 or one acetylamino in position 4, acetyloxy, preferably in position 2, the residue of an heterocycle with only one ring having 5 or 6 atoms which can be aromatic, partially or totally hydrogenated, containing one or more heteroatoms independently selected from O, N and S;

or $R_1$ has the meanings as defined for radical a) above, preferably ethoxy;

or $R_1$ is chosen from the following: phenyl; phenylamino in which the phenyl ring is optionally substituted with one or more halogen atoms, $C_1$-$C_3$ alkyl, preferably methyl, trifluoromethyl;

$R_2$ has the meaning as above defined for the radical a) substituent of $R_3$ when $R_3$ is an aromatic ring; and it can further have the following meanings:

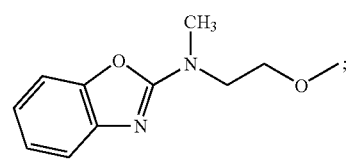
(AV-1)

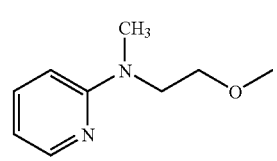
(AVI-1)

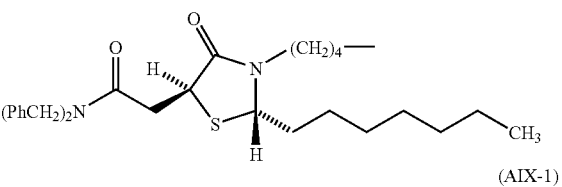
(AVIII-1)

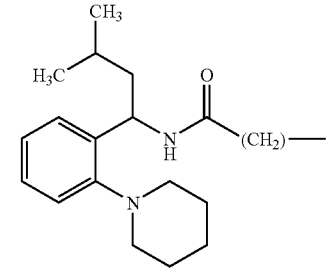
(AIX-1)

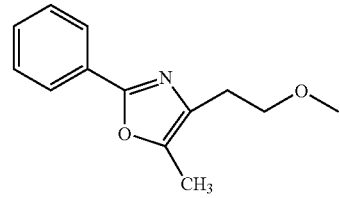
(ALXX-1)

wherein in formula (AV-1), (AVI-1) and (ALXX-1) the bond of $R_2$ with a carbon atom of the ring of formula (AII) occurs through the oxygen atom;

with the proviso that when $R_{XII}$=(AXL) $R_1$ and $R_2$ cannot be contemporaneously hydrogen;

M is one CH group or nitrogen;

wherein test 4A which must be met by the compound precursor of B, is a test in vitro wherein erythrocytes isolated by standard procedures from Wister male rats, are suspended at 4° C. for 4 days in a phisiological solution buffered at pH 7.4 with phosphate buffer; at the end, after having centrifuged at 1,000 rpm for 5 minutes a suspension aliquot, 0.1 ml of the erythrocytes centrifuged are diluted to 50 ml with sodium phosphate buffer pH 7.4, from which aliquots of 3.5 ml each (No. 5 samples) are taken and incubated at 37° C. in the presence of cumene hydroperoxide (270 µM in ethanol), which lysing the cells causes in the suspension a turbidity increase, which is determined at 710 nm at intervals of 30 minutes to establish the time (Tmax) at which there is the maximum hemolysis or maximum turbidity (100% of hemolysis); 2 mM ethanol solutions of the precursors of B are preincubated for 30 minutes with 3.5 ml aliquots of the diluted suspension of erythrocytes prepared after centrifugation (tests carried out on 5 samples for each precursor of B), then adding cumene hydroperoxide, and at the time Tmax determining the hemolysis percentage in the sample, expressed as ratio between the absorbance of the sample suspension and that of the suspension containing only cumene hydroperoxide; the precursors of B meet the test 4A if they inhibit the hemolysis induced by cumene hydroperoxide by a percentage >15%;

wherein test 5 is the following: it is an analytical determination carried out by adding aliquots of $10^{-4}$ M methanol solutions of the precursor of B to a solution containing a 2 mM solution of desoxyribose in water, 100 mM of phosphate buffer and 1 mM of the combined salt $Fe^{II}(NH_4)_2 (SO_4)_2$; after having thermostated the solution at 37° C. for one hour, aliquots of trichloroacetic acid 2.8% and of thiobarbituric acid 0.5 M are, in the order, added, heating is effected at 100° C. for 15 minutes and the absorbance of the tested solution is read at 532 nm; then the percentage of inhibition of the precursor of B towards the radical production is calculated by means of the formula:

$$(1-A_s/A_c)\times 100$$

wherein $A_s$ and $A_c$ are respectively the absorbance values of the solution containing the tested compound and the iron salt and that of the solution containing only the iron salt, the compound meets test 5 when the inhibition percentage as above defined of the precursor of B is higher than or equal to 50%;

wherein test 4 is the following: it is an analytical determination carried out by adding aliquots of methanol solutions at a $10^{-4}$ M concentration of the precursor of B to a methanol solution of DPPH (2,2-diphenyl-1-picryl hydrazyl); after having maintained the solution at room temperature and sheltered from light for 30 minutes, the absorbance of the test solution and of a solution containing only DPPH in the same amount, is read at the wave length oLf 517 nm; then the inhibition percentage of the precursor of B towards the radical production induced by DPPH is determined by means of the formula:

$$(1-A_s/A_c)\times 100$$

wherein $A_s$ and $A_c$ are respectively the absorbance values of the solution containing the test compound and DPPH and that of the solution containing only DPPH, the acceptance criterion of the compounds according to this test is the following: test 4 is satisfied by the precursor compounds of B when the inhibition percentage as above defined is higher than or equal to 50%.

The preferred compounds to be used as precursors of R are as herein below defined:

compounds of formula (AII) with $R_{XII}$=(AXL) and s=0 wherein:

when in formula (AII) M=CH, $R_1$ is hydrogen, and $R_2$ is an hydroxyl group in position 2 and the free valence is saturated with the COOH group, the compound is known as salicylic acid;

when in formula (AII) M=CH, $R_2$ is hydrogen, $R_1$ is $CH_3CONHCO$— and it is in position 2 of the ring and the free valence is saturated with an OH group, the compound is known as salacetamide;

when in formula (AII) M=CH, $R_2$ is $CONH_2$ and is in position 2 of the ring, $R_1$ is H and the free valence is saturated with an OH group, the compound is known as salicylamide;

when in formula (AII) M is nitrogen, $R_1$ is hydrogen, $R_2$ is methyl in position 3 of the ring and the free valence is saturated with a $NH_2$ group, the compound is known as 2-amino-picoline;

when in formula (AII) M=CH, $R_1$ is hydrogen, $R_2$ is a —$OSO_3H$ group in position 2 of the ring and the free valence is saturated with a COOH group, the compound is known as salicylsulphuric acid;

when in formula (AII) M=CH, $R_2$ is hydrogen, $R_1$ is a —$OCOR_3$ group with $R_3$=methyl, in position 2 of the ring and the free valence is saturated with a COOH group, the compound is known as acetylsalicylic acid;

when in formula (AII) M=CH, $R_2$ is a bromine atom in position 5, $R_1$ is a —$OCOR_3$ group with $R_3$=$CH_3$ in position 2 and the free valence is saturated with —COOH, the compound is known as 5-bromosalicylic acid acetate;

when in formula (AII) M=CH, $R_2$ is hydrogen, $R_1$ is in position 2 and is a —$OCOR_3$ group with $R_3$ equal to 2-(acetyloxy)phenyl and the free valence of the phenyl radical of formula (AII) is saturated with a COOH group, the compound is known as acetylsalicylsalicylic acid;

when in formula (AII) M=CH, $R_1$ is in position 2 and is the residue —OCOR3 wherein $R_3$ is 2-(hydroxy)phenyl, $R_2$ is hydrogen and the free valence is saturated with a COOH group, the compound is known as salsalate;

when in formula (AII) M=CH, $R_1$ is in position 2 and is the —$COOR_3$ residue, $R_3$ being phenyl, $R_2$ is hydrogen and the free valence is saturated with a OH group, the compound is known as phenylsalicylate;

when in formula (AII) M=CH, $R_1$ is in position 2 and is the —$COOR_3$ residue, $R_3$ being the 4-(acetylamino)phenyl group, $R_2$ is hydrogen and the free valence is saturated with the OH group, the compound is known as acetaminosalol;

when in Formula (AII), M=CH, $R_1$ is (3-trifluoromethyl)phenylamino group in position 2 of the ring, $R_2$=H and the free valence is saturated with the COOH group, the compound is known as flufenamic acid;

when in formula (AII), M=CH, $R_1$ is (2,6-dichloro-3-methylphenyl)amino group in position 2 of the ring, $R_2$=H and the free valence is saturated with the COOH group, the compound is known as meclofenamic acid;

when in formula (AII), M=CH, $R_1$ is (2,3-dimethylphenyl)amino group in position 2 of the ring, $R_2$=H and the free valence is saturated with the COOH group, the compound is known as mefenamic acid;

when in formula (AII), M=CH, $R_1$ is (3-chloro-2-methylphenyl)amino group in position 2 of the ring, $R_2$=H and the free valence is saturated with the COOH group, the compound is known as tolfenamic acid;

compounds of formula (AII) with $R_{XII}$=(AXL), and s=1 wherein:

when in formula (AII) $R_1$=H, $R_2$=—CH$_2$CH(CH$_3$)$_2$ in position 4 of the ring, M=CH and the free valence is saturated with COOH the compound is known as ibuprofen;

when in formula (AII), M=CH, $R_1$ is in position 4 of the ring and is phenyl, $R_2$ is a fluorine atom in position 3 and the free valence is saturated with the COOH group, the compound is known as flurbiprofen;

compounds of formula (AII) with $R_{XII}$=(AXX), M=nitrogen atom, $R_2$=H, $R_X$=(δ) wherein:

when $R_{14}$ of formula (AXX) is H and the free valence is saturated with COOH, the compound is known as niflumic acid;

when $R_{14}$ of formula (AXX) is CH$_3$ and the free valence is saturated with COOH, the compound is known as flunixin;

compounds of formula (AII) with $R_{XII}$=(AV), $R_X$=H, $R_2$ is (AV-1) at position 4 of the ring of formula (AII), M=CH, wherein:

when $R_{2p}$ of formula (AV)=CH$_3$ and the free valence is saturated with COOH, the compound is known as (S)-benzene propanoic acid, 4-[2-(2-benzoxazolyl-methylamino)ethoxy]-α-(2-ethoxy);

when $R_{2p}$ of formula (AV)=CF$_3$ and the free valence is saturated with COOH, the compound is known as (S)-benzene propanoic acid, 4-[2-(2-benzoxazolyl-methylamino) ethoxy]-α-(2,2,2-trifluoro ethoxy);

when in formula (AII) M=CH, $R_{XII}$=(AVI), $R_X$=H, $R_2$ is (AVI-1) at position 4 of the ring of formula (AII), the free valence is saturated with —COOH, the compound is known as L-tyrosine, N-(2-benzoyl phenyl)-O-[2-(methyl-2-pyridinylamino) ethyl];

when in formula (AII) M=CH, $R_{XII}$=(AX), $R_X$=$R_2$=H, the free valence is saturated with —COOH, the compound is known as mitiglinide;

when in formula (AII) M=CH, $R_{XII}$=(ALVX), $R_X$=$R_2$=H, the free valence is saturated with —COOH, the compound is known as nateglinide;

when in formula (AII) M=CH, $R_{XII}$=(ALXX) $R_X$=H, $R_2$=(ALXX-1) and is in position 4, the free valence is saturated with —COOH, the compound is known as farglitazar;

when in formula (AII) M=CH, $R_{XII}$=(AXL) and s=0, $R_1$=ethoxy; $R_2$=(AIX-1) in position 4, $R_1$=H, the free valence is saturated with —COOH, the compound is known as repaglinide;

when in formula (AII) M=CH, $R_{XII}$=(AXL) and s=0, $R_1$=H; $R_2$=(AVIII-1) in position 4, the free valence is saturated with —COOH, the compound is known as (2S,5S)-4-(4-(4-carboxy phenyl)butyl)-2-heptyl-4-oxo-5-thiazolidine N,N-dibenzyl acetamide;

when in formula (AII) M=CH, $R_2$=F and is in position 4, $R_X$ forms with $R_{XII}$ the radical of formula (AXXX) and the free valence is saturated with —COOH, the compound is known as sulindac;

prosta-5,9,12,14-tetraen-1-oic acid, 11-oxo-, (5Z,12E, 14E) (15-beoxy-Δ12,14-prostaglandin) of formula (AVII):

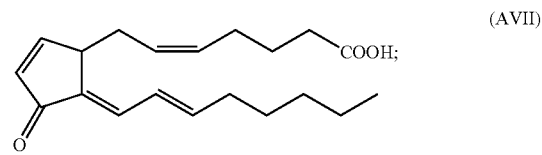

JTT-608 (4,keto-4-p.methylcyclohexyl-butyric acid)

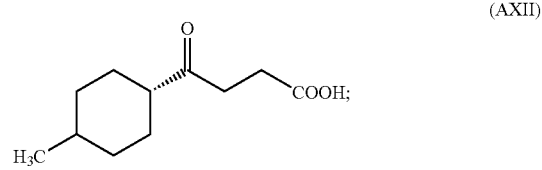

other compounds that can be used in the treatment of diabetes, preferably of type 2 diabetes, are the nitrate salts of the compounds of formula (AC):

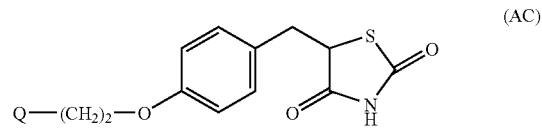

wherein Q is one of the two following substituents:

in (AC-1) the bond in position 2 of the pyridine ring indicates the site of attachement of Q to the aliphatic chain of formula (AC); the same for the bond on the tertiary aliphatic nitrogen atoms in (AC-2);

when Q is (AC-1) the compound is known as pioglitazione;

when Q is (AC-2) the compound is known as rosiglitazone.

The precursor compound of B (precursor of the radical $X_2$ in formula (I)) which meets test 4 is preferably selected from the following classes of compounds:

Aminoacids, selected from the following: L-carnosine, anserine, selenocysteine, selenomethionine, penicillamine, N-acetylpenicillamine, cysteine, N-acetylcysteine, glutathione or its esters, preferably ethyl or isopropyl ester;

Hydroxyacids, selected from the following: gallic acid, ferulic acid, gentisic acid, citric acid, caffeic acid, p-cumaric acid, vanillic acid;

Aromatic and heterocyclic mono- and polyalcohols selected from the following: nordhydroguaiaretic acid, quercetin, catechin, kaempferol, sulphurethyne, ascorbic acid, isoascorbic acid, hydroquinone, gossypol, reductic acid, metoxyhydroquinone, hydroxyhydroquinone, propyl gallate, saccharose, vitamin E 3,5-ditertbutyl-4-hydroxybenzylthio glycolate, p-cumaric alcohol, 4-hydroxyphenylethylalcohol, coniferyl alcohol;

Compounds containing at least a free acid function, selected from the following: 3,3'-thiodipropionic acid, fumaric acid, dihydroxymaleic acid, thioctic acid, edetic acid, bilirubin.

Preferably the precursor compound of B which meets test 5, is selected from the following compounds:

Aminoacids: aspartic acid, histidine, 5-hydroxy tryptophan, 4-thiazolidincarboxylic acid, 2-oxo-4-thiazolidin carboxylic acid;

Mono and polyalcohols or thiols: 2-thiouracil, 2-mercapto-ethanol, hesperidin, secalciferol, 1-α-OH vitamin D2, flocalcitriol, 22-oxacalcitriol, 24,28-methylene-1α-hydroxyvitamin D2;

Succinic acid.

In formula (I) the precursor compound of B which meet test 4A and do not meet test 5 are for example the following: 1,4-butandiol, 6-hydroxyhexanoic acid, 4-hydroxybutyric acid, N-methyldiethanolamine, diethylenglycol, thiodiethylenglicol, 1,4-dioxan-2,6-dimethanol, tetrahydropyran-2,6-dimethanol, 4H pyran-1,4-2,6-dimethanol, tetrahydrothiopyran-2,6-dimethanol, 1,4-dithiane-2,6-dimethanol, cyclohexene-1,5-dimethanol, thiazol-2,5-dimethanol, thiophene-2,5-dimethanol, oxa-zol-2,5-dimethanol, preferably N-methyldiethanolamine, dietilenglycol, thiodiethylenglycol.

The precursor compounds of B of the above mentioned groups are prepared according to the methods known in the prior art and described, for example in "The Merck Index, 12th Ed. (1996), herein incorporated by reference. When available, the corresponding isomers and optical isomers can be used. 24,28-methylene-1α-hydroxyvitamin D2 is prepared according to EP 578,494.

More specifically, the above reported tests are the following:

Test 4 is a calorimetric test which allows to establish whether the precursors of B are able to inhibit the production of radicals from DPPS (2,2-diphenyl-1-picryl-hydrazyl) (M. S. Nenseter et Al., Atheroscler. Thromb. 15, 1338-1344, 1995). 100 µM solutions in methanol of the tested substances are prepared and an aliquot of each of said solutions is added to a 0.1 M DPPH solution in methanol After having stored the solutions at room temperature and sheltered from light for 30 minutes the absorbance is read at the wave length of 517 nm. The absorbance decrease with respect to that of the solution containing the same DPPH concentration is determined. The effectiveness of the tested compound in inhibiting the production of radicals is expressed by the following formula:

$$(1-A_s/A_c) \times 100$$

wherein $A_s$ and $A_c$ are respectively the absorbance values of the solution containing the tested compound together with DPPH and of the solution containing only DPPH.

The precursor of B satisfies test 4 if its effectiveness in inhibiting the radical production, as above defined, is equal to or higher than 50% at the indicated concentration ($10^{-4}$ M).

Test 5 is a calorimetric test wherein 0.1 ml aliquots of solutions in methanol of the precursors of B at a concentration $10^{-4}$ M are added to a solution formed by 0.2 ml of 2 mM desoxyribose, 0.4 ml of phosphate buffer pH 7.4 100 mM and 0.1 ml of 1 mM $Fe^{II}(NH_4)_2(SO_4)_2$ in 2 mM HCl. The test tubes containing the reaction mixtures are then maintained at 37° C. for one hour. Then 0.5 ml of a 2.8% solution in water of trichloroacetic acid and 0.5 ml of an aqueous 0.1 M solution of thiobarbituric acid are added in the order in each test tube. A reference blank is formed by adding the same 0.1 ml aliquot of methanol without the tested compounds. The test tubes are closed and heated in an oil bath at 100° C. for 15 minutes. A pink coloration-develops the intensity of which is proportional to the oxidative degradation of the desoxyribose. The solutions are cooled at room temperature and their absorbance is determined at 532 nm. The inhibition percentage of the precursor of B towards the radical production is calculated by means of the formula:

$$(1-A_s/A_c) \times 100$$

wherein $A_s$ and $A_c$ are respectively the absorbance values of the solution containing the tested compound and the iron salt and that of the solution containing only the iron salt, the compound meets test 5 when the percentage of inhibition of radical production as above defined from the precursor of B is higher than or equal to 50%.

Test 4A is carried out according to the method described by R. Maffei Facino, M. Carini G. Aldini, M. T. Calloni, Drugs Exptl. Clin. Res. XXIII (5/8) 157-165 1997. Test 4A is a test in vitro wherein erythrocytes isolated by standard techniques from Wister male rats (Charles River), are suspended for 4 days at 4° C. in a phisiological solution buffered at pH 7.4 with phosphate buffer. After this period of time an aliquot of suspension is taken and centrifuged at 1,000 rpm for 5 minutes and 0.1 ml of the centrifuged erythrocytes are diluted to 50 ml with sodium phosphate buffer obtaining a suspension of erythrocytes 0.2% by volume. No. 5 aliquots of 3.5 ml each of the diluted suspension are incubated at 37° C. in the presence of cumene hydroperoxide (270 µM in ethanol). This compound causes cell lysis, which causes an increase of the suspension turbidity; cell lysis progress can be followed by turbidimetry at 710 nm, by performing the readings at intervals of 30 minutes so as to determine the time (Tmax) at which there is the maximum emolysis or maximum turbidity. The so determined Tmax is assumed to be the time corresponding to 100% of erythrocyte lysis. To determine the inhibition of the hemolysis induced by cumene hydroperoxide, 2 mM ethanol solutions of precursors of B are preincubated for 30 minutes with 3.5 ml aliquots of the erythrocyte suspension as above prepared (No. 5 samples for each compound precursor of B), cumene hydroperoxide is added in the same above mentioned amounts and the hemolysis percentage is determined in the sample at the Tmax as the ratio between the absorbance of the suspension of the tested sample and that of the suspension containing only cumene hydoperoxide; the precursors of B meet the test if they inhibit the haemolysis induced by cumene hydroperoxide by a percentage >15%.

Preferably Y³ is selected from the following:

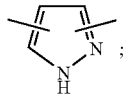 (Y1)

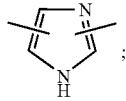 (Y2)

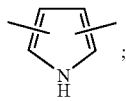 (Y3)

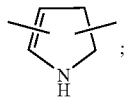 (Y4)

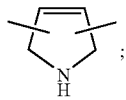 (Y5)

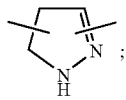 (Y6)

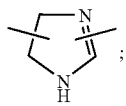 (Y7)

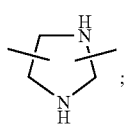 (Y8)

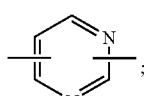 (Y9)

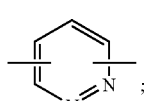 (Y10)

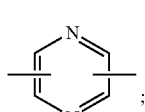 (Y11)

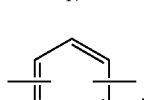 (Y12)

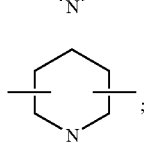 (Y13)

-continued

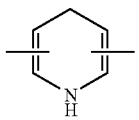 (Y14)

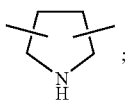 (Y15)

Preferably Y³ is an aroamtic ring having 6 atoms, containing one nitrogen atom, said aromatic ring having the two free valences respectively in positions 2 and 6, or 2 and 3 or 2 and 5 with respect to the heteroatom.

The preferred of Y³ is Y12 (pyridyl) substituted as above indicated. The bonds can also be in asymmetric position, for example Y12 (pyridyl) can be substituted also in position 2 and 3; Y1 (pyrazol) can be 3,5-disubstituted.

In general the precursor compounds of formula R=(AII) are well known in the art. The precursor compound of formula (AII) wherein $R_{XII}$=(AV) and $R_2$=(AV-1) can be prepared according to WO 97/25042. The compound of formula (AII) wherein $R_{XII}$=(AVI) and $R_2$=(AVI-1) can be prepared according to WO 97/31907. The precursor compound known as farglitizar can be prepared according to "Drugs of the future" 2001, 26(4) 354-363. The precursor compound of formula (AII) wherein $R_{XII}$=(AXL) with s=0 and $R_2$=(AVIII-1) can be prepared according to Proc. Natl. Acad. Sci 1999, 96(11) 6102. The precursor compound known as repaglinide is synthetized according to "Drugs of the future" 1996, 21, 694. The compounds known as mitiglinide, nateglinide, JTT-608 are synthetized according to "Drugs of the future" 2000, 25(10) 1034-1042, 694. The compounds pioglitazione and rosiglitazione can be synthetized according to "Drugs of the future" 1998 23(9) 977; the corresponding nitrate salts of these compounds can be prepared by obtaining said compounds in the free base form, then salified with nitric acid as described in WO 99/45004.

The compounds of formula (I) can be transformed into the corresponding salts. For example one route to prepare the salts is the following: when a nitrogen atom sufficiently basic to be salified is present in the molecule, the compound of formula (I) is reacted in organic solvent, such as for example acetonitrile, tetrahydrofuran, with an equimolecular amount of the corresponding organic or inorganic acid.

Examples of organic acids are: oxalic, tartaric, maleic, succinic, citric acid.

Examples of inorganic acids are: nitric, hydrochloric, sulphuric, phosphoric acid. Hydrochlorides and nitrates are preferred.

When in formula (I) c0=0 and b0=1 the preferred compounds are those wherein in radical R of formula (AII) with $R_{XII}$=(AXL), M=CH, s=0, $R_1$=H and $R_2$ is in position 2 of the aromatic ring and is OH, or $R_1$ is acetyloxy in position 2 of the ring and $R_2$=H, B is a residue of an aromatic polyalcohol, preferably a hydroxymethylphenol;

when in formula (I) c0=1 and b0=0 the preferred compounds are those wherein in the radical R of formula (AII) with $R_{XII}$=(AXL), M=CH, s=0, $R_1$=H and $R_2$ is in position 2 of the aromatic ring and is OH, or $R_1$ is acetyloxy in position 2 of the ring and $R_2$=H, C is $Y_p$ where $Y_p$ is preferably the residue of bis(hydroxymethyl)pyridine;

when in formula (I) c0=1 and b0=1 the preferred compounds are those wherein in radical R of formula (AII) with $R_{XII}$=(AXL), M=CH, and when:
s=0, $R_1$=H and $R_2$ is in position 2 of the aromatic ring and is OH or $R_1$ is acetyloxy in position 2 of the ring and $R_2$=H, B is the residue of the ferulic acid and Y is $Y_0$, preferably a $C_4$ alkylene,
s=1, $R_1$=H, $R_2$ is in position 4 of the aroamtic ring and is $CH_2CH(CH_3)_2$, B is the residue of N-acetylcysteine and Y is $Y_0$ preferably a $C_4$ alkylene.

The preferred compounds according to the present invention are those wherein the drug has formula (AII) and the compounds of formula (I) are the following: 2-acetyloxybenzoic acid 6-(nitrooxymethyl)-2-methylpyridinyl ester hydrochloride or nitrate, 2-acetyloxybenzoic acid 3-nitroxy methylphenyl ester, 2-acetyloxybenzoic acid 4-(nitrooxymethyl) phenyl ester, 2-acetyloxybenzoic acid 5-(nitrooxymethyl)-2-methylpyridinyl ester hydrochloride or nitrate, 2-(acetyloxy)benzoic acid 3-(nitrooxymethyl)-2-methyl pyridinyl ester hydrochloride or nitrate.

As said, the nitroderivatives of the invention are administered to patients suffering from diabetes both of type 1 and type 2, or in the cases wherein both are present (the so called intermediate diabetes forms). The compounds of the invention can also be administered to patients already under treatment with hypoglycemizing drugs, preferably insulin. The compounds of the invention are able to strengthen the direct antidiabetic effect, i.e. at a pancreatic level, and to reduce one or more diabete complications, in particular vascular and also retinopathies, neuropathies, gastroenteropathies, nephropathies complications, etc.

The compounds of the invention are particularly effective in the treatment of the type 2 diabetes, for which no commercial product has been found completely satisfactory.

The compounds of the invention are synthesized by the synthesis methods mentioned hereunder.

The choice of the reactions for each method depends on the reactive group present in the drug molecule, in the precursor compound of B, and in the precursor compound of C.

The reactions are carried out by methods well known in the prior art, which allow to obtain bonds among the drug, the precursor compound of B and the precursor compound of C as above defined.

When the reactive function of the drug (for example —CO—OH, —OH) is involved in a bond of covalent type, for example of ester, amide, ether type, said function can be restored by the well known methods in the prior art.

Some synthesis schemes for obtaining the compounds of the invention are reported hereinafter:

A) Synthesis of the compound of formula (I).
1. Synthesis of the compound obtained by reaction between the drug and the precursor compound of B.
1a. When the drug molecule contains a carboxylic function (general formula: R—COOH) and the functional group of the precursor compound of B which binds itself to the carboxylic function has XZ formula, X being as above defined and Z=H, the reactions which take place depend on the nature of the second reactive group present in the precursor compound of B.
1a.1 When the second reactive group present in the precursor compound of B is a carboxylic group, the synthesis general scheme expects the initial formation of the drug acylhalide R—COHal (Hal=Cl, Br) and the subsequent reaction with the HX group of the precursor compound of B:

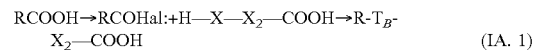

RCOOH→RCOHal:+H—X—$X_2$—COOH→R-$T_B$-$X_2$—COOH (IA. 1)

$X_2$, $T_B$ being as above defined.

When in the two compounds other functional groups COOH and/or HX are present, they must be protected before the reaction according to the methods known in the prior art; for example as described in the volume by Th. W. Greene: "Protective groups in organic synthesis", Harward University Press, 1980.

The RCOHal acylhalide is prepared according to the methods known in the prior art, for example by thionyl or oxalyl chloride, halides of $P^{III}$ or $P^V$ in solvents inert under the reaction conditions, such for example toluene, chloroform, DMF, etc.

In particular, if the HX group of the precursor compound of B is $NH_2$, or OH or SH, the drug of formula R—COOH is first converted into the corresponding acyl halide RCOHal, as above mentioned, and then reacted with the HX group of the precursor compound of B in the presence of an organic base, such as triethylamine, pyridine, etc. using a solvent inert under the reaction conditions such as toluene, tetrahydrofuran, etc. at a temperature in the range 0° C.-25° C.

Alternatively to the previous synthesis, the drug of formula R—COOH can be treated with an agent activating the carboxyl group selected from N,N'-carbonyldiimidazol (CDI), N-hydroxybenzotriazol and dicyclohexylcarbodiimide in solvent such as for example DMF, THF, chloroform etc. at a temperature in the range −5° C.-50° C. and the obtained compound reacted in situ with the reactive function of the precursor compound of B for obtaining the compound of formula (IA.1).

1a.2 When the precursor compound of B contains two functional groups XZ, equal to or different from each other, X being as above defined and Z=H, the drug of formula R—COOH is first treated with an agent activating the carboxyl group, as above described in 1a.1, and then with the precursor compound of B, after having protected one of the two reactive groups HX, for example with acetyl or ter-butyloxycarbonyl, restoring the initial function at the end of the synthesis. The scheme is the following:

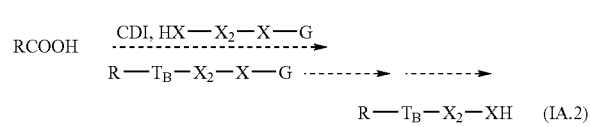

R—$T_B$—$X_2$—XH (IA.2)

wherein X, $T_B$, $X_2$ are as above defined and G is a protective group of the HX function.

Alternatively when the two functional groups of B are two hydroxyl groups, the synthesis scheme implies the initial formation of the drug acylhalide and the subsequent reaction with the precursor compound of B in the presence of a base, in an organic solvent inert under the reaction conditions according to the scheme reported below:

RCOHal+H—O—$X_2$—OH→R-$T_B$-$X_2$—OH (IA.2')

2. Synthesis of the nitroxyderivative.
2a.1 When the compound obtained at the end of the previous step 1a. has formula (IA.1), the acid can be converted into the corresponding sodium salt and then one can follow the methods known in the prior art for preparing the final compound, for example according to one of the following synthesis schemes:

A.)

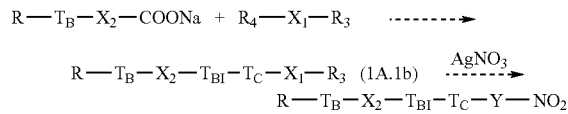

wherein $T_B$, $X_2$, $T_{BI}$, $T_C$ are as above defined, $R_4$ is selected from Cl, Br, Y is as above defined, $X_1$ is the Y without the oxygen atom, $R_3$ is Cl, Br, Iodine, OH. When $R_3$=OH the compound of formula (1A.1b) is subjected to halogenation, for example with $PBr_3$, $PCl_5$, $SOCl_2$, $PPh_3$+ $I_2$, and then reacted with $AgNO_3$ in organic solvent such acetonitrile, tetrahydrofuran. When $R_3$ is Cl, Br, Iodine, the compound of formula (1A.1b) is directly reacted with $AgNO_3$ as above mentioned.

$$R\text{-}T_B\text{-}X_2\text{—}COONa+Hal\text{-}Y\text{—}NO_2 \rightarrow R\text{-}T_B\text{-}X_2\text{-}T_{BI}\text{-}T_C\text{-}Y\text{—}NO_2 \quad \text{B.)}$$

C.)

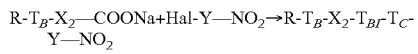

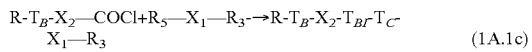

wherein $R_5$=OH or $NHR_{1C}$, $R_{1C}$, $R_3$ and the other symbols being as above defined.

When $X_1$ is a linear $C_4$ alkyl, the corresponding acid $R\text{-}T_B\text{-}X_2$—COOH is reacted with triphenylphosphine in the presence of an halogenating agent as $CBr_4$ or N-bromosuccinimide in tetrahydrofuran obtaining the compound (1A.1c) wherein $R_3$=Br.

2a.2 When the compound obtained at the end of the previous step 1a. has formula (IA.2), the corresponding nitroxyderivative is obtained by treating an halogencarboxylic acid of formula Hal-$X_1$—COOH, $X_1$ being as above defined, first with an agent activating the carboxyl group as described in 1A.1, and then with the compound of formula (Ia.2), obtaining an halogen derivative which is isolated and then dissolved in organic solvent, (ref. Paragraph 2a.1), and treated with silver nitrate. The global reaction scheme is the following:

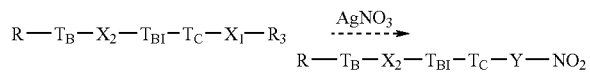

wherein $T_B$, $X_2$, $T_{BI}$, $T_C$, Y are as above defined.

Alternatively, the halide Hal-$X_1$—COCl can be used wherein Hal is preferably bromine, which is reacted with the compound of formula (IA.2)

2a.3 When the compound obtained at the end of step 1a.1 has formula IA2'), the corresponding nitroxyderivative can be obtained also by treating with fuming nitric acid under anhydrous conditions and in inert atmosphere, in the presence of an inorganic acid different from nitric acid, or with an organic acid, or of an anhydride of one or two organic acids.

1b. If the reactive function of the drug is —OH (general formula: R—OH), the two functional groups present on the precursor compound of B can be the following:

1b.1 A carboxylic group, which reacts with the OH function of the drug, and a HX group, the latter reactive group of the precursor compound of B being equal to or different from the drug functional group. The formula of the precursor compound of B is of the H—X—$X_2$—COOH type, wherein X and $X_2$ are as above defined.

The H—X— function of the precursor compound of B is protected according to known methods of the prior art and the carboxyl is reacted, as above indicated, according to the following scheme:

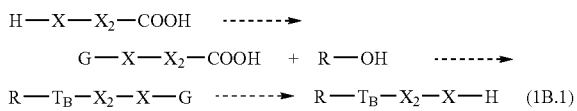

At the end of the reaction the HX function of the precursor compound of B is restored.

1b.2 When the precursor compound of B contains two carboxylic groups, it is treated with an equimolar amount of an agent activating the carboxyl group under the conditions previously described in 1a.1, and then reacted with the reactive OH function of the drug molecule. Possible other reactive functions of HX type present in the two compounds must be suitably protected as previously indicated. Lastly a compound of formula R-$T_B$-$X_2$—COOH (1B.2) is obtained.

2b. Synthesis of the nitroxyderivative.

2b.1 To obtain the final nitroxyderivative starting from the compound of formula R-$T_B$-$X_2$—X—H (1B.1), obtained at the end of the synthesis described in 1b.1, the compound (1B.1) is reacted with a halogenacid of formula Hal-$X_1$—COOH which has been treated as previously described in paragraph 1a.1, or with the corresponding halogenacid chloride, the resulting compound is dissolved in organic solvent, for example acetonitrile or tetrahydrofuran, and reacted with silver nitrate.

2b.2 To obtain the final nitroxyderivative starting from the compound of formula R-$T_B$-$X_2$—COOH (1B.2), obtained at the end of the synthesis described in 1b.2, the acid is transformed into the corresponding sodium salt, it is reacted with a compound $R_4$—$X_1$—$R_3$, previously defined in the reaction scheme A. of paragraph 2a.1, obtaining according to the same process therein reported the final nitroxyderivative. Alternatively, when $X_1$ is a linear $C_4$ alkyl, the acid (1B.2) is reacted with triphenylphosphine in the presence of an halogenating agent such as $CBr_4$ or N-bromosuccinimide in tetrahydrofuran and the resulting compound dissolved in organic solvent for example acetonitrile, tetrahydrofuran, is reacted with silver nitrate.

2b.3 Alternatively to the synthesis procedure according to 1b.1 and 2b.1, it is possible to react in a first step the HX— function of the precursor compound of B HX—$X_2$—COOH with the acyl chloride of a halogenacid of formula Hal-$X_1$—COCl, wherein Hal is preferably Br, and subsequently the carboxylic function of the so obtained compound, with the drug of formula R—OH. In the third and last step the -Hal group is substituted with —ONO$_2$ according to the process described in 2b.1. The reaction scheme is the following:

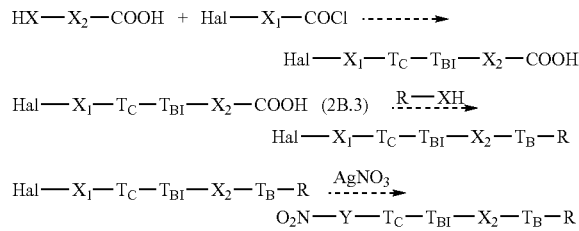

wherein $T_C$, $T_{BI}$, $T_B$, $X_2$, $X_1$, Y are as above defined.

In the previous scheme the nit ration can alternatively be carried out on the acid compound of formula (2B.3).

The compounds object of the present invention are formulated in the corresponding pharmaceutical compositions for parenteral, oral and topical use according to the techniques well known in the field, together with the usual excipients; see for example the volume "Remington's Pharmaceutical Sciences 15th Ed.".

The amount on a molar basis of the active principle in these formulations is the same, or lower, with respect to that used as antiinflammatory and/or analgesic drug of the corresponding precursor drug.

The daily administrable doses are those of the antiinflammatory and/or analagesic precursor drugs, or optionally lower. The daily doses can be found in the publications of the field, such as for example in "Physician's Desk reference".

The following Examples have the purpose to illustrate the invention and they are not to be considered as limitative of the same.

EXAMPLE 1

Synthesis of 2-acetoxybenzoic acid 6-(nitroxymethyl)-2-methylpyridinyl ester hydrochloride of formula

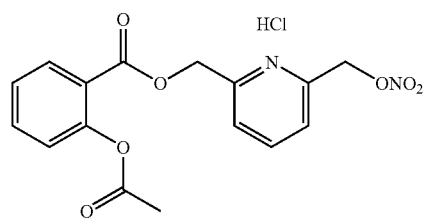

A) Synthesis of 2,6-bis-(chloromethyl)pyridine

To thionyl chloride (11.6 ml, 158 mmoles), cooled at 0° C., 2,6-bis-(hydroxymethyl)pyridine (4 g, 28 mmoles) is very slowly added. The obtained solution is left under stirring for 2 hours at room temperature, then the thionyl chloride in excess is evaporated at reduced pressure. The obtained residue is treated with chloroform and it is evaporated again at reduced pressure to eliminate the thionyl chloride residues. The crude product is treated with chloroform and washed with water. The organic phase is anhydrified with sodium sulphate and dried obtaining 4.81 g of the product as a white solid having m.p. 76-78° C.

B) Synthesis of 2-acetyloxybenzoic acid 6-(chloromethyl)-2methylpyridinyl ester

To a solution of acetylsalicylic acid (1.6 g, 8.88 mmoles) in N,N'-dimethylformamide (20 ml) and under stirring, sodium ethylate (0.64 g, 8.88 mmoles) is added. After 30 minutes the obtained solution is added to a solution of 2,6-bis-(chloromethyl)pyridine (4.72 g, 26.81 mmoles) in N,N'-dimethylformamide (20 ml). The solution is left at room temperature for 7 days, under stirring, then it is diluted with ethyl ether and washed with water. The separated organic phases are anhydrified with sodium sulphate and the solvent is evaporated at reduced pressure. The reaction crude product is purified by chromatography on silica gel eluting with n-hexane/ethyl acetate 7/3. 1.7 g of the product are obtained as a yellow oil.

$^1$H-NMR (200 MHz)(CDCl$_3$): 8.10 (1H,d); 7.74 (1H,t); 7.57 (1H,t); 7.42 (1H,d); 7.33 (2H,m); 7.11 (1H,d); 5.42 (2H,s); 4.67 (2H,s); 2.41 (3H, s).

C) Synthesis of 2-acetyloxybenzoic acid 6-(nitrooxymethyl)-2-methylpyridinyl ester To a solution of 2-acetyloxybenzoic acid 6-(chloro methyl)-2- methylpyridinyl ester (1.5 g, 4.7 mmoles) in acetonitrile (20 ml) maintained under stirring, silver nitrate (1.3 g, 7.65 mmoles) is added. The solution is heated at 80° C., maintaining it sheltered from light, under stirring for 30 hours. The formed silver chloride is filtered, the solvent is evaporated. The reaction crude product is purified by chromatography on silica gel eluting with n-hexane/ethyl acetate 7/3. 1.2 g of product are obtained as a yellow oil.

$^1$H-NMR (200 MHz) (CDCl$_3$): 8.10 (1H,d); 7.74 (1H,t); 7.57 (1H,t); 7.42 (1H,d); 7.33 (2H,m); 7.11(1H, d); 5.60(2H, s); 5.42 (2H, s); 2.41 (3H, s).

D) Synthesis of 2-acetyloxybenzoic acid 6-(nitrooxymethyl)-2-methylpyridinyl ester hydrochloride To a solution of 2-acetyloxybenzoic acid 6-(nitrooxymethyl)-2-methylpyridinyl ester (1 g, 2.88 mmoles) in ethyl acetate (20 ml) cooled at 0° C., a solution of ethyl acetate/HCl 5M is added by dropping under stirring. It is left for 1 hour at 0° C., then the temperature is let reach the room values. The formed precipitate is filtered and washed with ethyl ether. 900 mg of a solid product are obtained.

Elementary Analysis

| Calculated | C 50.21% | H 3.95% | N 7.31% | Cl 9.26% |
|---|---|---|---|---|
| Found | C 50.23% | H 3.97% | N 7.29% | Cl 9.20% |

$^1$H-NMR (200 MHz) (CDCl$_3$): 8.10 (2H,m); 7.7 (1H,t); 7.56 (2H,d); 7.48(1H,t); 7.30 (1H,d); 5.74 (2H,s); 5.43 (2H,s); 2.20 (3H, s)

EXAMPLE 2

Synthesis of 3-nitrooxymethylphenyl ester of the 2-acetoxybenzoic acid

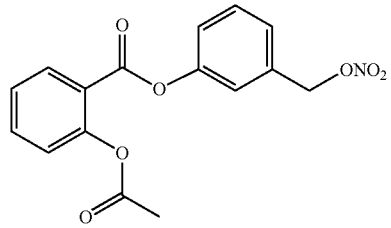

A) Preparation of 3-hydoxymethylphenyl ester of the 2-acetoxybenzoic acid 3-hydroxymethylphenol (10 g, 0.08 moles) is dissolved in toluene (50 ml) containing triethylamine (9.8 g, 0.1 moles). To the so obtained solution, a solution of the acetylsalicylic acid chloride (16 g, 0.08 moles) in toluene (50 ml) is added at the temperature of 5-10° C. under stirring. The mixture is maintained at a temperature within the above mentioned range, under stirring for 2 hours, then poured in water and then extracted with dichloromethane (2×100 ml) The organic phase is separated, washed in sequence with a solution of potassium carbonate at 25% w/v, with water, with a 3% hydrochloric acid solution, and lastly again with water, then anhydrified with sodium sulphate and the solvent evaporated under vacuum. The residue is crystallized from isopropanol. 3-hydroxymethylphenyl ester of the 2-acetoxybenzoic acid (45.8 g, 0.16 moles, yield 80%) is obtained.

M.p. 79-81° C. $^1$H NMR(CDCl$_3$) δ (ppm): 2.29 (s,3H); 4.71 (s,2H); 7.07-8.2 (m, aromatic compounds, 8H).

B) Nitration of 3-hydroxymethylphenyl ester of the 2acetoxybenzoic acid

A solution of fuming nitric acid (3.92 g, 62.2 mmoles, 3 moles with respect to the moles of the hydroxyester under reaction) and sulphuric acid 96% (6.10 g, 62.2 mmoles, 3 moles with respect to the moles of the hydroxyester under reaction) in dichloromethane (25 ml) is cooled at 0° C. and added in 1 hour time, under stirring and under nitrogen atmosphere, with a solution of 3-hydroxymethylphenyl ester of the 2-acetoxybenzoic acid (6 g, 20.7 mmoles) in 25 ml of dichloromethane. The mixture is then diluted with dichloromethane (50 ml) and poured in water and ice (100 g) The organic phase is separated, washed with water, anhydrified with sodium sulphate and the solvent evaporated under vacuum. The residue is crystallized from isopropanol obtaining the 3-nitrooxymethylphenyl ester of the 2-acetoxybenzoic acid (5.6 g, 17 mmoles, yield 82%).

M.p. 61-62° C. $^1$H NMR(CDCl$_3$) δ (ppm): 2.31 (s,3H); 5.44 (s,2H); 7.16-8.22 (m, aromatic compounds, 8H).

EXAMPLE 3 COMPARATIVE

Synthesis or 1-(4-chlorobenzoyl)-5-methoxy-2-methyl-3-indolacetic acid 3'-(nitroxymethyl)phenyl ester

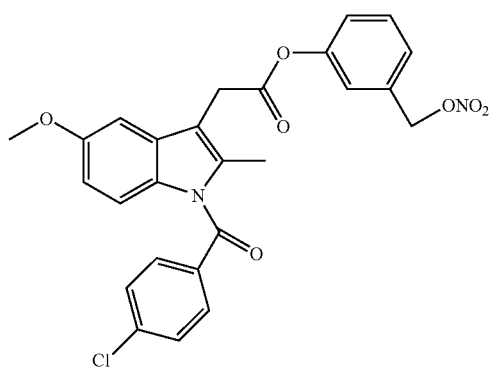

A) Synthesis of 1-(p-chlorobenzoyl)-5-methoxy-2-methyl-3-indolacetic acid 3'-formylphenyl ester To a solution of 1-(p-chlorobenzoyl)-5-methoxy-2-methyl-3-indolacetic acid (20.08 g, 56.12 mmoles) in chloroform (200 ml) and dimethylformamide (20 ml), 3-hydroxybenzaldehyde (6.82 g, 55.85 mmoles), N,N'-dicyclohexyl carbodiimide (11.6 g, 56.22 mmoles) and N,N-dimethylamino pyridine (0.306 g, 2.5 mmoles) are in the order added. The mixture is maintained under stirring at room temperature for 6 hours. The precipitate is filtered and the organic phases are washed with water (100 ml×2), anhydrified with sodium sulphate and the solvent is evaporated at reduced pressure. The crude product is purified by chromatography on silica gel eluting with methylene chloride. 20.99 g of 1-(p-chlorobenzoyl)-5-methoxy-2-methyl-3-indolacetic acid 3'-formylphenyl estere are obtained. Yield 81%.

B) Synthesis of 1-(p-chlorobenzoyl)-5-methoxy-2-methyl-3-indolacetic acid 3-(hydroxymethyl)phenyl ester A solution of 1-(p-chlorobenzoyl)-5-methoxy-2-methyl-3-indolacetic acid 3'-formylphenyl ester (20 g, 4.33 mmoles) in ethyl acetate (200 ml) is hydrogenated in the presence of palladium 5% on carbon (2 g) at room temperature under stirring, using an hydrogen pressure of about 2.5 atm. After 30 minutes the reactor is discharged removing the catalyst by filtration under nitrogen atmosphere. The solvent is evaporated at reduced pressure and the residue is purified by chromatography on silica gel eluting with methylene chloride/acetic acid (95:5 v/v). 14 g of 1-(p-chlorobenzoyl)-5-methoxy-2-methyl-3-indolacetic acid 3'-(hydroxymethyl)phenyl ester are obtained as a yellow solid. Yield 73%.

C) Synthesis of 1-(p-chlorobenzoyl)-5-methoxy-2-methyl-3-indolacetic acid 3'-(chloromethyl)phenyl ester To a solution of 1-(p-chlorobenzoyl)-5-methoxy-2-methyl-3-indolacetic acid 3'-(hydroxymethyl)phenyl ester (13 g, 2.81 mmoles) in chloroform (200 ml) and cooled by an ice bath, a solution of SOCl$_2$ (2.06 ml, 2.81 mmoles) in chloroform (50 ml) is added. The mixture is maintained under stirring for 30 minutes in ice bath and for 20 hours at room temperature. The solution is washed first with a bicarbonate solution and then with water. The organic phase is anhydrified with sodium sulphate and the solvent is evaporated at reduced pressure. The residue is purified by chromatography on silica gel eluting with methylene chloride/hexane (1:1 v/v). 9.86 g of 1-(p-chlorobenzoyl)-5-methoxy-2-methyl-3-indolacetic acid 3'-(chloromethyl)phenyl ester are obtained as a yellow solid.

M.p. 147-150° C. Yield 73%.

D) Synthesis of 1-(p-chlorobenzoyl)-5-methoxy-2-methyl-3-indolacetic acid 3'-(nitrooxymethyl)phenyl ester To a solution of 1-(p-chlorobenzoyl)-5-methoxy-2-methyl-3-indolacetic acid 3'-(chloromethyl)phenyl ester (9.86 g, 2.04 mmoles) in acetonitrile (100 ml) silver nitrate (4.87 g, 2.87 mmoles) is added and the mixture is heated at 80° C. under stirring for 15 hours. It is cooled, the precipitate is filtered and the solvent is evaporated at reduced pressure. The residue is purified by chromatography on silica gel eluting with methylene chloride/hexane (1:1 v/v). 9.83 g of 1-(p-chlorobenzoyl)-5-methoxy-2-methyl-3-indolacetic acid 3'-(nitrooxymethyl)phenyl ester are obtained. M.p. 115-119° C.

Yield 94.5%. $^1$H NMR (CDCl$_3$) 7.70 (2H,d); 7.49 (2H,d); 7.42 (1H,t); 7.14-7.06 (4H,m); 6.90 (1H,d); 6.70 (1H,dd); 5.42 (2H,s); 3.93 (2H,s); 3.86 (3H,s); 2.48 (3H,s).

EXAMPLE 4

Synthesis of (S)-N-acetyl-{α-methyl[4-(2-methylpropyl) benzene] acetyl}cysteine 4-(nitroxy)butyl ester

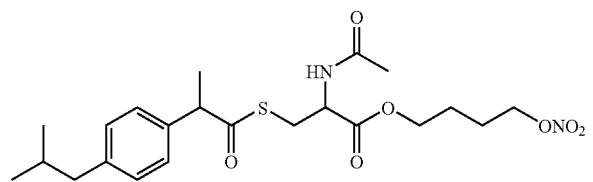

A) Synthesis of (S)-N-acetyl-{α-methyl[4-(2-methylpropyl) benzene]acetyl}cysteine To a solution of α-methyl[4-(2-methylpropyl)benzene] acetic acid (10 g, 48.48 mmoles) in chloroform (100 ml) and N,N-dimethylformamide (6 ml) 1,1'-carbonyldiimidazol (7.86 g, 48.48 mmoles) is added. After 1 hour the obtained solution is treated with (S)-N-acetylcysteine (7.91 g, 48.47 mmoles) and it is left at room temperature for 24 hours. The reaction mixture is washed with HCl 5%, then with water and lastly with brine. The organic phase is anhydrified with sodium sulphate and then evaporated at reduced pressure. The obtained residue is purified by chromatography on silica gel eluting with ethyl acetate. 13.3 g of the expected product are obtained under the form of an oil.

$^1$H-NMR (CDCl$_3$) : 10.17 (1H,s) 7.13 (2H,d) 6.54 (1H,d), 4.76 (1H,m), 3.93 (1H,q), 3.42-3.30 (2H,m), 2.49 (2H,d), 1.85-1.83 (4H,m), 1.55 (3H,d), 0.93 (6H, d)

B) Synthesis of (S)-N-acetyl-{α-methyl[4-(2-methylpropyl)benzene]acetyl}cysteine 4-(bromobutyl) ester To a solution of (S)-N-acetyl-S-{α-methyl[4-(2-methylpropyl)benzene]acetyl}cysteine (12.8 g, 36.4 mmoles) in tetrahydrofuran (100 ml), triphenylphosphine (28.65 g, 109.23 mmoles) and carbon tetrabromide (36.23 g, 109.23 mmoles) are added. The reaction mixture is left under stirring for 48 hours at room temperature. The solvent is removed by evaporation at reduced pressure. The obtained crude product is purified by chromatography on silica gel eluting with cyclohexane/ethyl acetate 1/1. 5.79 g of the ester are obtained in the form of an oil.

C) Synthesis of (S)-N-acetyl-{α-methyl[4-(2-methylpropyl) benzene]acetyl}cysteine 4-(nitroxy)butyl ester To a solution of the ester obtained at the end of the previous step (5.5 g, 11.3 mmoles) in acetonitrile (100 ml), silver nitrate (2.69 g, 15.8 mmoles) is added. The reaction mixture is heated for 24 hours under reflux sheltered from light. The formed salt is removed by filtration and the solution is evaporated at reduced pressure. The obtained residue is purified by chromatography on silica gel eluting with cyclohexane/ethyl acetate 7/3. 1.18 g of (S)-N-acetyl-{α-methyl[4-(2-methylpropyl)benzene]acetyl}cysteine 4-(nitroxy)butyl ester are obtained under the form of an oil.

$^1$H-NMR (CDCl$_3$) : 7.27-7.09 (4H,m), 6.19 (1H,d), 4.75 (1H,m), 4.47 (2H,t), 4.15-4.02 (2H,m), 3.86 (1H,q), 3.31 (2H,d), 2.44 (2H,d), 1.89 (3H,d), 1.86-1.76 (SH, m), 1.51 (3H,d), 0.89 (6H,d).

Elementary Analysis:
Calculated C: 56.39% H: 6.88% N: 6.00% S: 6.84%
Found C: 56.22% H: 6.79% N: 5.88% S: 6.92%

EXAMPLE 5

Synthesis of trans-3-[4-[2-(acetyloxy)benzoyloxy]-3-methoxyphenyl]-2-propenoic acid 4-(nitroxy) butyl ester

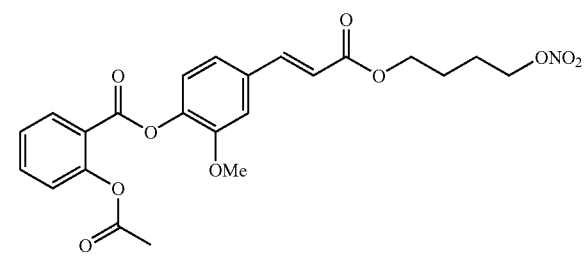

A) Synthesis of trans-3-[4-hydroxy-3-methoxyphenyl]-2-propenoic acid 4-bromo butyl ester To a solution of ferulic acid (10 g, 51.5 mmoles) in THF (400 ml), cooled in a water bath, triphenylphosphine (27.01 g, 103 mmoles) and carbon tetrabromide (34.1 g, 103 mmoles) are in the order added. The mixture is maintained under stirring for 5 hours at room temperature. When the reaction is over, the formed triphenylphosphinoxide is filtered and the solvent is evaporated at reduced pressure. The residue is purified by chromatography on silica gel eluting with hexane/ethyl acetate (7:3 v/v). 7.75 g of trans-3-[4-hydroxy-3-methoxyphenyl]-2-propenoic acid 4-bromobutyl ester are obtained as a white solid. M.p. 86-89° C. Yield 46%.

B) Synthesis of trans-3-[4-[2-(acetyloxy)benzoyloxy]-3-methoxyphenyl]-2-propenoic acid 4-bromobutyl ester To a solution of trans 3-[4-hydroxy-3-methoxyphenyl]-2-propenoic acid 4-bromo butyl ester (2 g, 6.1 mmoles) in CHCl₃ (20 ml), a mixture of acetyl salicylic acid (1.1 g, 6.1 mmoles) in DMF (2 ml) is added and cooled at 0° C. Then DCC (1.50 g, 7.2 mmol) and DMAP (74 mg, 6×10⁻³ mmoles) are added. The solution is left at the same temperature for 30 minutes and then it is let reach the room temperature, maintaining this last temperature for 16 hours. The precipitate is filtered and the solvent is evaporated at reduced pressure. The residue is dissolved in ethyl acetate (100 ml×2 times) and washed with water and NaCl. The organic phase is anhydrified and the solvent is evaporated at reduced pressure.

The residue is purified by chromatography on silica gel eluting with hexane/ethyl acetate (8:2 v/v), obtaining the trans-3-[4-[2-(acetyloxy)benzoyloxy]-3-methoxyphenyl]-2-propenoic acid 4-bromobutyl ester (1.1 g, Yield 37%).

$^1$H NMR: 8.25 (1H,d); 7.65 (2H,m); 7.40 (1H,t); 7.20 (4H,m); 6.39 (1H,d); 4.25 (2H,t); 3.85 (3H,s); 3.47 (2H,t); 2.29 (3H, s); 2.01 (2H,m); 1.89 (2H,m):

C) Synthesis of trans-3-[4-[2-(acetyloxy)benzoyloxy]-3-methoxyphenyl]-2-propenoic acid 4-nitroxybutyl ester To a solution of 3-[4-[2-(acetyloxy) benzoyloxy]-3-methoxyphenyl]-2-propenoic acid 4-bromobutyl ester-(1 g, 2.03 mmoles) in acetonitrile (10 ml), silver nitrate (0.530 g, 3.11 moles) is added, under stirring, sheltered from light. It is heated at 80° C. for 8 hours and at the end it is cooled at room temperature. The precipitate is filtered and the solvent is evaporated at reduced pressure.

The residue is purified by chromatography on silica gel eluting with hexane/ethyl acetate (7:3 v/v) obtaining 3-[4-[2-(acetyloxy)benzoyloxy]-3-methoxyphenyl]-2-acid 4-nitroxybutyl ester (506 mg) as a white solid. Yield 52.6%.

$^1$H NMR: 8.24 (1H, d); 7.65 (2H, m); 7.39 (1H, t); 7.18-7.14 (4H, m); 6.39 (1H, d); 4.51 (2H, t); 4.25 (2H, t); 3.85 (3H, s); 2.95 (3H, s); 1.89-1.82 (4H, m).

EXAMPLE 6

Synthesis of 2-(acetyloxy)benzoic acid 4-(nitroxymethyl) phenyl ester

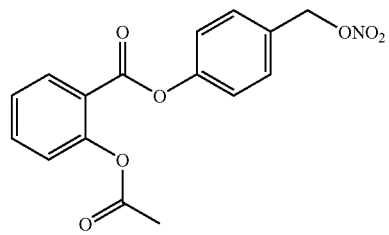

A) Synthesis of 2-(acetoxy)benzoic acid 4-(formyl)phenyl ester

To a mixture of 4-hydroxybenzaldehyde (20.75 g, 0.17 moles) and triethylamine (0.205 g, 2.4 mmoles) in methylene chloride (300 ml) maintained under stirring under inert nitrogen atmosphere, cooled at a temperature between −5° C. and 0° C., acetylsalicyloil chloride (41.25 g, 0.21 moles) is added by small parts in one hour time. After 15 minutes from the addition completion, water (250 ml) is added and the phases are separated. The aqueous phase is recovered and extracted with methylene chloride. The organic phases are put together, washed with a carbonate solution at 5% (150 ml×2) and then with water (125 ml×2). The organic phase is anhydrified with sodium sulphate in the presence of decolorizing carbon. It is filtered under vacuum and the solvent is evaporated at reduced pressure with a bath temperature not higher than 40° C., obtaining 48.2 g of 2-(acetyloxy)benzoic acid 4-(formyl)phenyl ester. The reaction crude product is used without further purification.

B) Synthesis of 2-(acetyloxy)benzoic acid 4-(hy-droxymethyl) phenyl ester

A solution of 2-(acetyloxy)benzoic acid 4-(formyl)phenyl (48.2 g, 0.18 moles) ester in ethyl acetate (500 ml) is hydrogenated in the presence of 5% palladium on carbon (4 g) at room temperature under stirring, using an hydrogen pressure of about 2.5 atm. After 30 minutes the reactor is discharged and the catalyst is removed by filtration under nitrogen atmosphere.

The organic phase is washed with a 5% sodium, bicarbonate solution and with water. It is anhydrified with sodium sulphate and the solvent is evaporated at reduced pressure. The residue is used without further purification.

C) Synthesis of 2-(acetyloxy)benzoic acid 4-(chloromethyl) phenyl ester

To a mixture of 2-(acetyloxy)benzoic acid 4-(hydroxy methyl)phenyl (51.5 g, 0.18 moles) and SOCl₂ (153 ml) maintained under stirring, dimethyl formamide (140 ml) is added at room temperature and it is left under stirring for one hour. At the end the thionyl chloride is evaporated at reduced pressure at a bath temperature lower than 40° C. The thionyl chloride traces in the compound are removed by treating the solid residue with toluene (60 ml×2). The solvent is removed by evaporation at reduced pressure with a bath temperature lower than 40° C. The crude product is. purified by crystallization with isopropyl ether to give 2-(acetyloxy)benzoic acid 4-(chloromethyl)phenyl ester (32.9 g, 0.10 moles). Yield 60%.

$^1$H NMR: 8.25 (1H,d); 7.68 (1H,t); 7.43 (3H,m); 7.20 (3H,m); 4.60 (2H,s); 2.34 (3H,s).

D) Synthesis of 2-(acetyloxy)benzoic acid 4-(ni-troxymethyl) phenyl ester

To a solution of 2-(acetyloxy)benzoic acid 4-(chloromethyl)phenyl, ester (32.9 g, 0.10 moles) in acetonitrile, silver nitrate (22.2 g, 0.12 moles) is added, under stirring, sheltered from light. It is heated at 70° C. for 4 hours and then cooled at room temperature. The precipitate is filtered and the solvent is evaporated at reduced pressure.

The residue is purified by chromatography on silica gel eluting with hexane/ethyl acetate (7:3 v/v) to give 2-(acetyloxy)benzoic acid 4-(nitroxymethyl)phenyl ester (16.6 g, 0.05 moles). M.p. 86-88° C. Yield 50%.

$^1$H NMR (CDCl$_3$): 8.21 (1H,dd); 7.66 (1H,dt); 7.42 (3H,m); 7.20 (3H,m); 5.40 (2H, s), 2.25 (3H,s)

PHARMACOLOGICAL EXAMPLES

EXAMPLE F1

To evaluate the strengthening effect of the drugs of the invention on the antidiabetic activity of insulin, animals (rats) are treated with a fructose rich diet (Am. J. Physiol. 275, R788-R792, 1998). In this way an insulinic resistance is induced in the animals. Under such conditions the animal does not respond any longer to the usual insulin doses.

The pharmacological test is a test in vitro and consists in determining the vasorelaxing activity induced by the products of the invention, measured on an isolated vessel (aorta) taken from animals treated as above mentioned. The test in vitro is carried out both in the presence and in absence of LNNA (N-nitro-L-Arginine), which is an irreversible inhibitor of the nitric oxide synthethases, to verify if the vasorelaxing effect depends on the protective endogenous substances (nitric oxide).

The capability of the compounds of the invention to exert a vasorelaxing effect both in the presence and in absence of vasoprotective substances in such conditions of experimental diabetes, (animals with a fructose rich diet, and treated with or without LNNA), is an index which allows to evaluate the antidiabetic action of the tested compound.

In the pharmacological experiment isolated vessels are used, taken from rats which have developed, as said, an insulinic resistance condition induced by administering for 4 weeks a fructose rich diet.

Preparation of Tissues

Male Sprague Dawley rats having an average weight equal to 150-200 g were sacrificed and bled. The abdominal aorta was removed and suitably prepared for determining the myorelaxing activity in vitro according to the method described by Vogel G. H. et al., Drug Discovery Evaluation-Pharmacological Assays page 32, 1996.

A part of the specimen is treated with LNNA.

The tissues are precontracted with phenylephrine (10 μM) and the relaxation was determined in the presence or in absence of the compounds of the invention or of the reference standards. The compounds were dissolved in dimethylsulphoxide and tested at doses which do not meaningfully modify the vascular tone in the non insulin resistant animal (subjected to normal diet). The results are reported in Table 1 and are expressed as a percentage with respect to the vasorelaxing effect measured in the controls.

In Table 1 the compound of comparative Example 3 is the indomethacin ester with m-nitrooxymethylphenol, the compound of Example 6 is the acetylsalicylic acid ester with p-nitrooxymethylphenol, the compound of Example 2 is the acetylsalicylic acid ester with m-nitrooxymethylphenol, the compound of Example 1 is the acetylsalicylic acid ester with 6-(nitrooxymethyl)-2-hydroxymethyl pyridine.

The results of the pharmacological test contained in the Table show that the compounds of the invention are able to induce a vasorelaxing effect both in the presence and in absence of vasoprotective substances (nitric oxide) in conditions of experimental diabetes.

The indomethacin ester (Example 3 comp.) and the sodium nitroprussiate, both NO-donor compounds, on the contrary, did not result active.

The metformin, which is a drug used in the diabetes therapy, is active only in the absence of the inhibitor of the NO synthesis.

TABLE 1

Determination in vitro on the aorta of insulin-resistant rats of the vasorelaxing effect. The results are expressed as percentages with respect to the non insulin-resistant controls.

| Treatment | Concentration (M) | % Relaxation Aorta Without LNNA | Aorta with LNNA |
|---|---|---|---|
| Carrier | — | 45 | 10 |
| Compound Ex. 3 comp. | $10^{-6}$ | 20 | 20 |
| Sodium Nitroprussiate Comp. | $10^{-6}$ | 30 | 30 |
| Compound Ex. 6 | $10^{-5}$ | 90 | 65 |
| Compound Ex. 2 | $10^{-4}$ | 70 | 70 |
| Compound Ex. 1 | $10^{-5}$ | 93 | 70 |
| Metformin Comp. | $10^{-4}$ | 90 | 30 |

The invention claimed is:

1. A method of treating type 2 diabetes comprising administering to a subject a compound or salt thereof of the following formula:

A-(B)$_{b0}$-(D)$_{c0}$-NO$_2$     (I)

wherein c0 is an integer and is 0 or 1;

b0 is an integer and is 0 or 1; with the proviso that at least one between c0 and b0 is different from zero;

A=R-T$_1$-, wherein R-T$_1$- is a radical or a precursor drug acetylsalicylic acid of formula R-T$_1$-OH, wherein T$_1$=(CO); and R is a remaining radical of acetylsalicylic acid;

B=T$_B$-X$_2$-T$_{BI}$- wherein

T$_B$=X, wherein X=O, S, N or NR$_{1C}$, wherein R$_{1C}$ is H or a linear or branched alkyl having from 1 to 5 carbon atoms;

T$_{BI}$=(CO) or X, wherein X is as above defined; and $X_2$ is a radical of a compound of formula $H-X_2-H$ selected from the following compounds:

hydroxyacids, selected from the group consisting of: gallic acid, ferulic acid, gentisic acid, citric acid, caffeic acid, p-cumaric acid and vanillic acid;

D is a bivalent radical $-T_c-Y-$ wherein:
when b0 is 1, $T_c=(CO)$ when $T_{BI}=X$, or $T_c=X$ when $T_{BI}=(CO)$, wherein
X is as above defined;
when b0 is 0, $T_c=X$ wherein X is as above defined;
Y is:
$Y_p$:

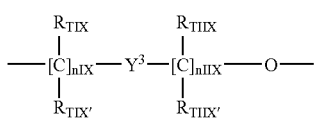
(III)

wherein:
nIX is an integer in the range 0-3;
nIIX is an integer in the range 1-3;
$R_{TIX}$, $R_{TIX'}$, $R_{TIIX}$, $R_{TIIX'}$, equal to or different from each other are H or linear or branched $C_1$-$C_4$ alkyl,
$Y^3$ is a saturated, unsaturated or aromatic heterocyclic ring containing one or two nitrogen atoms, having 6 atoms;
$Y_O$, which is selected from the group consisting of:
an alkylenoxy group R' wherein R' is $C_1$-$C_{20}$ linear or branched; or
one of the following groups:

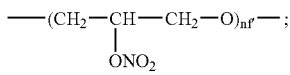

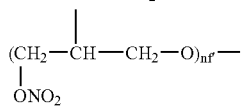

wherein nf' is an integer from 1 to 6;

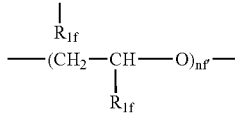

wherein $R_{1f}$=H, $CH_3$ and nf is an integer from 1 to 6; or
$Y_{Ar}$, which is selected from the group consisting of:

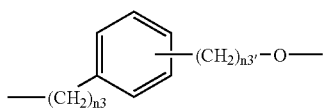

wherein n3 is an integer from 0 to 3 and n3' is an integer from 1 to 3;

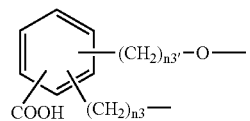

wherein n3 and n3' have the above indicated meaning; and
when b0=1 then c0=1 and Y is $Y_O$; or
when b0=0 then c0=1 and Y is $Y_p$ or $Y_{Ar}$.

2. The method of claim 1, wherein $R_{TIX}$, $R_{TIX'}$, $R_{TIIX}$ and $R_{TIIX'}$ are H and $Y^3$ in the formula (III) is selected from the group consisting of:

(Y1)

(Y2)

(Y3)

(Y4)

(Y5)

(Y6)

(Y7)

(Y8)

(Y9)

(Y10)

-continued

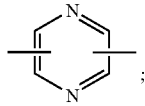 (Y11)

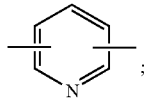 (Y12)

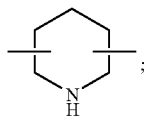 (Y13)

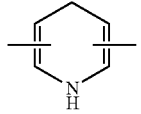 (Y14)

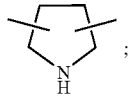 (Y15)

wherein $Y^3$ is an aromatic ring having 6 atoms, containing one nitrogen atom, and having the two free valences respectively in position 2 and 6, or 2 and 3, or 2 and 5 with respect to the heteroatom.

3. The method of claim 2, wherein $Y^3$ is Y12 substituted in position 2 and 6, having bonds also in asymmetric position.

4. The method of claim 1, wherein:

when c0=1 and b0=0, D is $Y_p$; or

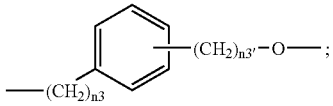

when in c0=1 and b0=1, $X_2$ is ferulic acid or N-acetyl-cysteine.

5. The method of claim 1, wherein the compounds are selected from the group consisting of: 2-acetyloxybenzoic acid 6-(nitrooxymethyl)-2-methylpyridinyl ester hydrochloride or nitrate, 2-acetyloxybenzoic acid 3-nitroxy methylphenyl ester, 2-acetyloxybenzoic acid 4-(nitrooxymethyl) phenyl ester, 2-acetyloxybenzoic acid 5-(nitrooxymethyl)-2methyl pyridinyl ester hydrochloride or nitrate, 2(acetyloxy) benzoic acid 3-(nitrooxymethyl)-2-methyl pyridinyl ester hydrochloride or nitrate, and trans 3-[4-(2-acetyloxy) benzoyloxy]-2-metoxyphenyl]-2-propenoic acid 4-(nitroxy) butyl ester.

6. The method of claim 1, wherein the compounds are transformed into corresponding salts of the compounds.

7. The method of claim 1, wherein the compounds, or their salts, are used in the corresponding pharmaceutical formulations for parenteral, oral and topical use.

8. The method of claim 1, wherein the compounds are administered to patients already under treatment with hypoglycemizing drugs selected from the group consisting of insulin and metformin.

9. The method of claim 8, wherein the hypoglycemizing drug is insulin.

10. A method of reducing or treating vascular disease, retinopathy, neuropathy, gastroenteropathy, or nephropathy associated with type 2 diabetes comprising administering to a subject a compound selected from the group consisting of: 2-acetyloxybenzoic acid 6-(nitrooxymethyl)-2-methylpyridinyl ester hydrochloride or nitrate, 2-acetyloxybenzoic acid 3-nitroxy methylphenyl ester, 2-acetyloxybenzoic acid 4-(nitrooxymethyl) phenyl ester, 2-acetyloxybenzoic acid 5-(nitrooxymethyl)-2methyl pyridinyl ester hydrochloride or nitrate, 2-(acetyloxy) benzoic acid 3-(nitrooxymethyl)-2-methyl pyridinyl ester hydrochloride or nitrate, and trans 3-[4-(2-acetyloxy)benzoyloxy]-2-metoxyphenyl]-2-propenoic acid 4-(nitroxy)butyl ester.

* * * * *